United States Patent [19]

Ramprasad et al.

[11] Patent Number: 5,744,636

[45] Date of Patent: Apr. 28, 1998

[54] PROCESS FOR THE PRODUCTION OF ETHYLIDENE DIACETATE FROM DIMETHYL ETHER USING A HETEROGENEOUS CATALYST

[75] Inventors: Dorai Ramprasad; Francis Joseph Waller, both of Allentown, Pa.

[73] Assignee: Air Products and Chemicals, Inc., Allentown, Pa.

[21] Appl. No.: 651,130

[22] Filed: May 21, 1996

[51] Int. Cl.$^6$ .................................................. C07C 67/00
[52] U.S. Cl. ........................................................ 560/204
[58] Field of Search ..................................... 560/190, 204

[56] References Cited

U.S. PATENT DOCUMENTS

| | | | |
|---|---|---|---|
| 4,328,125 | 5/1982 | Drago et al. | 252/426 |
| 4,429,150 | 1/1984 | Drent | 560/232 |
| 5,155,261 | 10/1992 | Marston et al. | 562/519 |
| 5,354,886 | 10/1994 | Park et al. | 560/232 |
| 5,360,929 | 11/1994 | Watson et al. | 562/891 |
| 5,364,963 | 11/1994 | Minami et al. | 562/519 |
| 5,371,274 | 12/1994 | Park et al. | 560/232 |
| 5,371,275 | 12/1994 | Park et al. | 560/232 |

FOREIGN PATENT DOCUMENTS

| | | |
|---|---|---|
| 0028474 | 5/1981 | European Pat. Off. . |
| 0566371A2 | 4/1993 | European Pat. Off. . |
| 51-115409 | 3/1976 | Japan . |

OTHER PUBLICATIONS

Advanced Inorganic Chemistry, 5th Edition, p. 1272, 1986.
Jarrell and Gates, J. Catal., 40, 255 (1975).

*Primary Examiner*—Samuel Barts
*Attorney, Agent, or Firm*—Keith D. Gourley

[57] ABSTRACT

This invention relates to a process for producing ethylidene diacetate by the reaction of dimethyl ether, acetic acid, hydrogen and carbon monoxide at elevated temperatures and pressures in the presence of an alkyl halide and a heterogeneous, bifunctional catalyst that is stable to hydrogenation and comprises an insoluble polymer having pendant quaternized heteroatoms, some of which heteroatoms are ionically bonded to anionic Group VIII metal complexes, the remainder of the heteroatoms being bonded to iodide. In contrast to prior art processes, no accelerator (promoter) is necessary to achieve the catalytic reaction and the products are easily separated from the catalyst by filtration. The catalyst can be recycled for 3 consecutive runs without loss in activity.

19 Claims, No Drawings

PROCESS FOR THE PRODUCTION OF ETHYLIDENE DIACETATE FROM DIMETHYL ETHER USING A HETEROGENEOUS CATALYST

This invention was made with Government Support under Contract No. DE-FC22-95PC93052 between Air Products and Chemicals, Inc., and the U.S. Department of Energy. The Government has certain rights to this invention.

TECHNICAL FIELD OF THE INVENTION

This invention relates to a process for producing ethylidene diacetate by hydrocarbonylating dimethyl ether in the presence of a heterogeneous, bifunctional catalyst that is stable to hydrogenation. The catalyst contains quaternized heteroatoms, some of which heteroatoms are ionically bonded to anionic Group VIII metal complexes, the remainder being bonded to iodide.

BACKGROUND OF THE INVENTION

Ethylidene diacetate (EDA) is a valuable chemical because it is a precursor to vinyl acetate monomer. There are a number of homogeneous catalytic processes for the production of EDA. Representative processes for preparing EDA include the process disclosed in U.S. Pat. No. 4,429,150 in which methyl acetate and/or dimethyl ether (DME), CO and $H_2$ are reacted in the presence of a catalyst system comprising a Group VIII metal and a halogen containing compound in the presence of a sulfur-containing polar solvent. Japanese Patent No. 51-115409 and European Patent No. 0028474 and 0566371A2 disclose processes for producing EDA using homogeneous rhodium catalysts. All these processes suffer from the significant disadvantage of requiring separation and purification of the reaction products from the homogeneous catalyst.

To solve this problem, U.S. Pat. No. 5,371,274 discloses a process for making EDA using a heterogeneous catalyst of the general formula $M_aX$, where M is a rhodium phosphine complex covalently bound to an organic carrier X. The product was produced by reacting methyl acetate, iodomethane, CO and $H_2$ in the presence of this supported catalyst and an accelerator such as 3-picoline at elevated temperature and pressure. The product of the reaction is easily separated from the heterogeneous catalyst but the accelerator still has to be separated from the product. In addition to this, it is well known that rhodium phosphine complexes covalently bound to an organic polymer tend to leach out rhodium (See Advanced Inorganic Chemistry, 5th Edition, p 1272). The organic polymer used to support rhodium in U.S. Pat. No. 5,371,274 is a standard kind of phosphine containing polymer used to support rhodium and has been described in detail by Jarrell and Gates, *J. Catal.*, 40, 255 (1975). They report that the catalyst lost activity rapidly due to rhodium leaching from the support even at low temperatures in the range of 85°–95° C. In U.S. Pat. No. 5,371,275 and U.S. Pat. No. 5,354,886 rhodium complexes supported on an inorganic carrier such as silica or alumina and used to make EDA are disclosed.

Many others have attempted to design heterogeneous catalysts with a view of minimizing the leaching of the metal complex. One such system is described in U.S. Pat. No. 4,328,125 as an anion exchange resin to which is ionically bound an anionic metal carbonyl species having the general formula $M_n(CO)_m(X)_p^-$, where M is a transition metal. These catalysts have been described and used for the carbonylation of alcohols for the production of carboxylic acids. Marston et al. in U.S. Pat. No. 5,155,261 and Minami et al. in U.S. Pat. No. 5,364,963 have described a similar catalyst consisting of a cross-linked 4-vinylpyridine divinylbenzene copolymer containing quaternized pyridine groups supporting a rhodium species. This catalyst is robust and offers higher operating temperatures for the carbonylation of methanol to acetic acid. U.S. Pat. No. 5,360,929 discloses the use of such polymeric pyridine catalysts to produce carboxylic acid anhydrides from carboxylate esters and ethers. No mention is made about using such catalysts, however, for EDA production from the reaction of methyl acetate or dimethyl ether with CO and $H_2$ gas.

SUMMARY OF THE INVENTION

A process for producing EDA is disclosed wherein dimethyl ether (DME) is hydrocarbonylated in the presence of a heterogeneous, bifunctional catalyst under conditions sufficient to form EDA. The process comprises reacting DME, hydrogen, carbon monoxide, acetic acid, and an alkyl halide in the presence of the bifunctional catalyst. The catalyst comprises an insoluble polymer having pendant quaternized heteroatoms, some of which heteroatoms are ionically bonded to anionic Group VIII metal complexes, the remainder of the heteroatoms being bonded to iodide.

Use of a bifunctional catalyst of the present invention for EDA production has distinct advantages over the use of other catalysts (U.S. Pat. No. 5,371,274) in that accelerators like 3-picoline are not required and the separation of catalysts from product is made easier. The use of ionic bonding to the Group VIII metal complex also offers a further advantage in that the leaching of metal from the catalyst is minimized. The process is highly selective toward EDA, can be completed under short reaction times at high temperatures and pressures, and can proceed with recycling of the catalyst.

DETAILED DESCRIPTION OF THE INVENTION

The present invention provides a process for making EDA from DME, hydrogen ($H_2$), carbon monoxide (CO), and acetic acid (HOAc) in the presence of an alkyl iodide and a bifunctional catalyst that is stable to hydrogenation and comprises an insoluble polymer having pendant quaternized heteroatoms, some of which heteroatoms are ionically bonded to anionic Group VIII metal complexes, the remainder of the heteroatoms being bonded to iodide, under conditions sufficient to form EDA. The formed EDA is then recovered.

The bifunctional catalyst is a heterogeneous catalyst that contains an insoluble polymer having quaternized heteroatoms. The quaternized heteroatoms are quaternized by techniques well known in the art using an alkyl halide. Preferred alkyl halides contain from one to six carbon atoms (e.g., lower alkyl). Preferred halides are iodide (I), chloride (Cl) or bromide (Br) and, more preferably iodide. A most preferred alkyl halide is methyl iodide.

The polymer is an organic polymer that renders the catalyst insoluble in organic solvents. The polymer must be large enough and be sufficiently cross-linked to be insoluble. Organic polymers suitable for use as substrates for catalysts are well known (See, e.g., U.S. Pat. No. 5,155,261, the disclosure of which is incorporated herein by reference). The polymer component of catalysts described in that patent are cross-linked vinylpyridine resins such as resins sold under the trade name Reillex™ by Reilley Tar and Chemical Corporation. Particularly suitable such vinylpyridine resins are Reillex™ 425 and Reillex™ HP, both of which are a poly-4-vinylpyridine cross-linked to divinylbenzene. Still other suitable polymers for use in a bifunctional catalyst are described in U.S. Pat. No. 5,364,963, the disclosure of which is incorporated herein by reference. This patent describes improved cross-linked vinylpyridine resins. The improved resins have a degree of cross-linking between about 30 and 60%. The vinylpyridine resins described in U.S. Pat. No. 5,364,963 are prepared by copolymerizing a vinylpyridine monomer with an aromatic compound having two vinyl groups as a cross-linking agent. Exemplary suitable cross-linking agents are aromatic divinyl compounds such as divinylbenzene and divinyl toluene. Suitable vinylpyridines of the polymer include 4-vinylpyridine, 2-vinylpyridine and 2- and 4-vinylpyridine derivatives having a lower alkyl group such as a methyl group or ethyl group on the pyridine ring. Such vinylpyridine monomers can be used in conjunction with aromatic vinyl monomers such as styrene or vinyl toluene. The most preferred polymers are those available under the Reillex™ family of trademarks from Reilley Tar & Chemical Corporation of Indianapolis, Ind. and contain heteroatoms capable of being quaternized with an alkyl halide.

As is well known in the art, heteroatoms capable of being quaternized with alkyl halides include nitrogen (N), sulfur (S), oxygen (O) and phosphorus (P). A preferred heteroatom for use in a bifunctional catalyst of the presently claimed invention is N. The N atom is preferably part of a pendant free base including tertiary amines, secondary amines, pyridines, or any nitrogen heterocycle group. The N can be substituted or unsubstituted.

Following quaternization of the polymer heteroatoms (e.g., refluxing the polymer with an excess of methyl iodide in toluene), the polymer is ionically attached to anionic Group VIII metal complexes. The catalyst of the present invention utilizes a Group VIII metal selected from the group consisting of rhodium (Rh), platinum (Pt), palladium (Pd), iridium (Ir), ruthenium (Ru), cobalt (Co), and nickel (Ni). Preferred Group VIII metals are Rh, Ir and Pd. Rh is most preferred.

The Group VIII metal catalyst used in the catalyst system is present in a catalytically effective amount and such catalytically effective amounts can be readily determined by those of ordinary skill in the art. The amount of Group VIII metal to be incorporated into the catalyst system typically ranges from about 0.01 mol % to about 10 mol % based on the DME present, preferably from 0.03 to about 5 mol %.

In a preferred embodiment, an anionic Group VIII metal complex corresponds to the general formula $[M(CO)_aL_bX_c]^-$ where M is Rh, Ir or combinations thereof; L is an alkyl or acyl group; X is a halide ion; a is 1, 2, 3 or 4; b is 0 or 1; and c is 2 or 3. The sum of a, b and c is equal to or less than six (i.e., a+b+c≦6).

In another preferred embodiment, an anionic Group VIII metal complex corresponds to the general formula $[M(CO)_aL_bX_c]^{-2}$ where M is Pd; L is an alkyl or acyl group; X is a halide ion; a is 1, 2, 3 or 4; b is 0 or 1; and c is 2 or 3. The sum of a, b and c is equal to or less than six (i.e., a+b+c≦6).

In a preferred embodiment, M is Rh, X is Cl, a is ≦4, b is 0, c is 2, the formula of the Group VIII metal complex is $Rh_2(CO)_4Cl_2$, and the anionic species $[Rh(CO)_2I_2]^-$ is incorporated into the polymer.

Using the Rh complexes described above, the maximum Rh content that can be incorporated into the polymer is 16.9% by weight of the polymer or less. Because the catalyst used in a process of the present invention is bifunctional, it is important that only a portion of the quaternized heteroatoms be ionically bonded to the anionic Group VIII metal complex. By way of example, where the Group VIII metal is Rh, the total content of Rh in the catalyst is less than 16.9% by weight of the polymer. As shown hereinafter in the Examples, catalysts having between about 2% and 6% by weight of Rh have been successfully used in the preparation of EDA.

The quaternized heteroatoms not ionically bonded to the anionic Group VIII metal complex are bonded to iodide ($I^-$). This bonding of I to the catalyst eliminates the need for any extraneous promoter or accelerator in the overall reaction of making EDA from DME.

The term hydrocarbonylation, as referred to herein, refers to the reaction of DME, acetic acid, hydrogen and carbon monoxide to form EDA under the enumerated process conditions. Hydrocarbonylation can be carried out in a batch mode or a continuous mode over a wide range of temperatures. While the optimum temperature for practicing the present invention will depend upon process stoichiometry, the particular catalyst system utilized, as well as the precise combination of reaction conditions, suitable hydrocarbonylation temperatures will range from about 90° C. up to about 225° C. However, the most preferred hydrocarbonylation temperatures range from about 170° C. to about 210° C. The hydrocarbonylation reaction can be carried out under a wide variety of pressures including pressures ranging from about 500 psig to about 3000 psig. Preferred pressures range from about 1000 psig to about 2000 psig. Most preferred reaction conditions are a temperature of 190° C. and a pressure of 1500 psig. The products of the reaction are analyzed by gas chromatography at various times during the reaction and also in a batch mode (i.e., at the end of the reaction). The catalyst can be removed by filtration and reused for a new feed without a loss in initial activity.

Carbon monoxide and hydrogen are present in the reaction mixture in a stoichiometric ratio of greater than 40:60. Preferably, that stoichiometric ratio ranges from 40:60 to 90:10. Even more preferably, that stoichiometric ratio is 80:20.

The desired product (EDA) is recovered from the product mixture which includes acetic acid and other reaction products. As will be evident from this Specification, the present invention provides a convenient route for co-producing EDA and acetic acid.

Reaction time is not critical in practicing the present invention and one of ordinary skill in the art can determine optimum reaction times based upon the enumerated reaction conditions, catalyst system and catalyst concentration presented herein. Reaction times required to produce a desired amount of EDA will also depend upon the reaction temperature and pressure. Typically, reaction times range from 0.5 hours to 4.0 hours.

In contrast to prior art processes, no accelerator is necessary to achieve the catalytic reaction and the products are easily separated from the catalyst by filtration. The catalyst can be recycled without loss in activity. The catalysts of the present invention are well suited toward use in the process for making EDA presented in U.S. Pat. No. 5,502,243.

The following examples are presented to further illustrate the scope of the present invention and are not intended to limit the scope thereof.

EXAMPLE 1

Preparation of Heterogeneous Catalyst

A sample of Reillex™ 425 (24 g) was dried in an oven at 100° C. for 14 hours. The dried polymer beads were placed in a flask which contained 125 ml of toluene and the mixture was refluxed for 30 minutes under nitrogen. After cooling to room temperature, 20 ml of methyl iodide was added and the resulting mixture was heated at 95° C. for 48 hours and then stirred at room temperature for another 5 days. The yellow beads/powder was filtered and dried under vacuum for 8 hours.

Approximately 0.36 g of the Group VIII metal complex $Rh_2(CO)_4Cl_2$ was dissolved in 100 ml of toluene. About 3.36 g of quaternized Reillex™ prepared in the previous step was added, the mixture was stirred for approximately 24 hours and the powder was filtered. No color was observed in the filtrate indicating that all the rhodium was on the polymer. The Reillex™ material contained about 5.1% by weight of rhodium. By using this method and by varying the amount of complex, a 2.24% Rh containing polymer was also prepared. These experiments were repeated using a Reillex™ high-porosity (HP) polymer.

The samples were characterized by infrared spectroscopy, and showed two strong carbonyl bands at 2056 and 1984 cm−1, which bands are characteristic of the species $[Rh(CO)_2IX]^-$, where X=Cl or I and prove that the rhodium is attached ionically to the polymer.

EXAMPLE 2

Catalyst Evaluation and Recycle

A 300 cc Hastelloy C autoclave was equipped with a dip tube for loading DME from a pre-weighed cylinder, thermocouple, belt driven stirrer, and an inlet for gases. Another tube at the bottom of the reactor equipped with a frit was used to remove samples for analysis during the reaction. The autoclave was charged with DME (0.176 mol), methyl iodide (0.062 mol), acetic acid (2.28 mol), 3.35 g of Reillex™ 425 having 2.24% Rh and $CO/H_2$ in a 1:1 stoichiometric ratio. The reaction was run at 190° C. and 1500 psig and samples were taken at 5, 10, 20, 30, and 45 min. respectively and analyzed by gas chromatography. The catalyst was removed by filtration at the end of the reaction and reused for two more runs using a fresh charge of reactants (recycled).

The results of these studies are summarized below in Table 1.

TABLE 1

Results of Catalytic Runs at 45 min. With Recycle

| Exp. No | Catalyst Wt(g) | % Rh | Conv$^a$ (%) | Sel (%) EDA | Mass Bal$^c$ (%) |
|---|---|---|---|---|---|
| 1 | 3.35 | 2.24 | 99.6 | 18.4 | 92.6 |
| 2 | Recycle | 2.24 | 99.8 | 35.5 | 93.3 |
| 3 | Recycle | 2.24 | 100 | 24.3 | 86.9 |

$^a$Conv (%) = Conversion = [DME reacted]/[DME]t,
$^b$Sel EDA (%) = Selectivity of EDA = {2[EDA]/[DME reacted]}
$^c$Mass balance = {2[EDA] + [DME] + [MeOAc] + [Ac₂O] + [CH₄]}/[DME]t The data show that the selectivity towards EDA does not decrease below the initial value. These data also show that the catalyst can be recycled and that leaching of rhodium is not a significant problem. Similar studies were performed using the analogous homogeneous catalytic reaction with rhodium chloride. In these latter studies, no EDA was formed in the absence of added promoter (e.g., lithium iodide). These findings show that no added accelerator or promoter is required with the use of the bifunctional catalyst.

EXAMPLE 3

Comparison of Heterogeneous Catalytic Runs With and Without Addition of Promoter The same autoclave, as used in Example 2, was charged with DME (0.24 mole), acetic acid (2.42 mol), methyl iodide (0.063 mol) and 1.47 g of Reillex™ 425 containing 2.01% of rhodium by weight. The autoclave was pressurized with a 1:1 mix of $CO/H_2$ and the reaction was run at 1500 psig and 190° C. Samples were collected at 5, 10, 20, and 30 minutes respectively. The selectivity for EDA was about 3.5% at 30 minutes. The Reillex™ material was filtered and analyzed to give a Rh load of 1.63%. The gain in weight of the polymer was attributed to additional sites being quaternized with methyl iodide.

The catalytic reaction was repeated with a fresh batch of Reillex™ 425 containing 2.01 % by weight of rhodium, only this time an additional 1.5 g of the promoter lithium iodide (LiI) was added. The selectivity to EDA at 30 minutes was similar, but an elemental analysis of the catalyst after the reaction showed only 0.588% by weight of rhodium. These data show that some of the rhodium leached from the catalyst into the solution. Thus, it is a disadvantage to run the reactions with accelerators (promoters) when using a bifunctional catalyst of the present invention.

EXAMPLE 4

Batch Results of Catalytic Runs

The procedure described in Example 2 was followed except for the fact that no samples were taken during the experiment. The reactor was cooled at the end of the run and the products were analyzed by gas chromatography. The results are shown below in Table 2.

TABLE 2

| Polymer | Wt(g) | Rh(%) | Time(min.) | Conv(%) | Sel EDA (%) | Mass Bal* |
|---|---|---|---|---|---|---|
| Reillex ™ 425 | 1.5 | 2.24 | 60 | 100 | 20.4 | 85.5 |
| Reillex ™ 425 | 1.5 | 2.24 | 120 | 100 | 35.1 | 74.4 |
| Reillex ™ 425 | 0.65 | 5.1 | 120 | 100 | 35.5 | 91* |
| Reillex ™ HP | 1.5 | 2.24 | 60 | 100 | 22.1 | 93.3* |
| Reillex ™ HP | 1.5 | 2.24 | 120 | 100 | 36 | 89* |

*MASS BAL INCLUDES METHANE

The results show that both the Reillex™ 425 and Reillex™ HP, with comparable Rh loading, gave similar selectivities towards EDA. A higher selectivity toward EDA was obtained by increasing the time of reaction from 60 min. to 120 min. A Reillex™ 425 with a 5.1% Rh loading behaved similarly to a 2.24% Rh loading provided that the overall amount of rhodium used was the same. Finally, better mass balances were obtained when methane was included in the calculation.

EXAMPLE 5

Recycle Studies

The same autoclave as used in Example 2 was charged with acetic acid (1.2 mol), DME (0.12 mol), methyl iodide (0.03 mol), and $CO/H_2$ (1:1). The reaction was run at 1500 psig and at 190° C. for 2 hours with catalyst recycling. Products were removed via the frit, but the catalyst was left in the reactor. Product concentrations were determined via gas chromatography. The experiment was repeated three times. The results are summarized below in Table 3.

TABLE 3

| Exp. No. | Conv. (%) | MeOAc (%) Sel | Ac Sel (%) Ac₂O | EDA Sel (%) |
|---|---|---|---|---|
| 1 | 99.1 | 16.9 | 19.5 | 47.6 |
| recycle | 99.3 | 15.2 | 9.6 | 49.5 |
| recycle | 99.3 | 9.2 | 26.4 | 46.8 |
| recycle* | 99.4 | 9.2 | 20 | 46.8 |

*Mass balances in eighties for all runs

The results demonstrate that a bifunctional catalyst of the present invention can be recycled without loss of product (EDA) yield or selectivity.

What is claimed is:

1. A process for producing ethylidene diacetate which comprises reacting dimethyl ether, hydrogen, carbon monoxide and acetic acid in the presence of an alkyl iodide and a bifunctional catalyst that is stable to hydrogenation and comprises an insoluble polymer having pendant quaternized heteroatoms, some of which heteroatoms are ionically bonded to anionic Group VIII metal complexes, the remainder of the heteroatoms being bonded to iodide, under conditions sufficient to form EDA and recovering the formed EDA.

2. The process according to claim 1 wherein the Group VIII metal complex contains rhodium, palladium or iridium.

3. The process of claim 2 wherein the anionic Group VIII metal complex contains rhodium.

4. The process according to claim 3 wherein the anionic Group VIII metal complex has the formula $[Rh(CO)_2I_2]^-$.

5. The process of claim 1 wherein the quaternized heteroatom is nitrogen.

6. The process according to claim 1 wherein the alkyl iodide is methyl iodide.

7. The process of claim 1 wherein the insoluble polymer is a 4- or 2-vinylpyridine cross-linked with divinylbenzene.

8. The process according to claim 1 wherein the reaction conditions comprise a temperature ranging from 90° C. to 225° C., a pressure ranging from 500 psig to 3000 psig, and a reaction time ranging from 0.5 hours to 4 hours.

9. The process according to claim 8 wherein the temperature ranges from 170° C. to 210° C. and the pressure ranges from 1000 psig to 2000 psig.

10. The process according to claim 9 wherein the temperature is 190° C. and the pressure is 1500 psig.

11. The process according to claim 1 wherein carbon monoxide (CO) and hydrogen ($H_2$) are present in a stoichiometric ratio ($CO:H_2$) of from 40:60 to 90:10.

12. The process according to claim 11 wherein the stoichiometric ratio of carbon monoxide to hydrogen is 80:20.

13. The process according to claim 1 wherein the catalyst is prepared by reacting an insoluble polymer having quaternized heteroatoms with a Group VIII metal compound of the formula $[M(CO)_aL_bX_c]^-$, where M is Rh or Ir, or combinations thereof; L is an alkyl or acyl group; X is a halide ion; a is 1, 2, 3 or 4; b is 0 or 1; and c is 2 or 3, where $a+b+c \leq 6$.

14. The process according to claim 1 wherein the catalyst is prepared by reacting an insoluble polymer having quaternized heteroatoms with a Group VIII metal compound of the formula $[M(CO)_aL_bX_c]^{2-}$, where M is Pd; L is an alkyl or acyl group; X is a halide ion; a is 1, 2, 3 or 4; b is 0 or 1; and c is 2 or 3, where $a+b+c \leq 6$.

15. The process of claim 13 wherein M is Rh, X is Cl, a is $\leq 4$, b is 0 and c is 2.

16. The process of claim 14 wherein M is Pd, X is Cl, a is $\leq 4$, b is 0 and c is 2.

17. A process for producing ethylidene diacetate which comprises reacting dimethyl ether, hydrogen, carbon monoxide and acetic acid in the presence of methyl iodide and a bifunctional catalyst that is stable to hydrogenation and comprises an insoluble polymer having quaternized pyridine groups, some of which pyridine groups are ionically bonded to $[Rh(CO)_2I_2]^-$, the remainder of the pyridine groups being bonded to iodide, under conditions sufficient to form EDA and recovering the formed EDA.

18. The process according to claim 17 wherein the reaction conditions comprise a temperature ranging from 90° C. to 225° C. and a pressure ranging from 500 psig to 3000 psig.

19. The process according to claim 18 wherein the temperature is 190° C. and the pressure is 1500 psig.

* * * * *